United States Patent
Morinaka

(10) Patent No.: US 6,345,910 B1
(45) Date of Patent: Feb. 12, 2002

(54) METHOD OF DETERMINING THE MAGNESIUM CONTENT IN MOLTEN ALUMINUM ALLOYS

(75) Inventor: Mayuki Morinaka, Shizuoka (JP)

(73) Assignee: Metal Science Ltd. (JP)

( * ) Notice: Subject to any disclaimer, the term of this patent is extended or adjusted under 35 U.S.C. 154(b) by 0 days.

(21) Appl. No.: 09/510,260

(22) Filed: Feb. 22, 2000

(30) Foreign Application Priority Data

Feb. 24, 1999 (JP) .......................................... 11-089504

(51) Int. Cl.$^7$ .......................... G01N 25/00; C22C 33/00
(52) U.S. Cl. ............... 374/45; 374/26; 420/18
(58) Field of Search ................. 374/45, 26; 420/528, 420/18, 129; 148/549

(56) References Cited

U.S. PATENT DOCUMENTS

| | | | | |
|---|---|---|---|---|
| 3,662,173 A | * | 5/1972 | Youmans | 250/269.8 |
| 4,358,948 A | * | 11/1982 | Plessers | 374/26 |
| 4,454,230 A | * | 6/1984 | Denney | 422/61 |
| 4,592,538 A | * | 6/1986 | Wells, III | 266/216 |
| 4,667,725 A | * | 5/1987 | Backerud | 164/4.1 |
| 4,913,878 A | * | 4/1990 | Dawson et al. | 420/18 |
| 5,305,815 A | * | 4/1994 | Pan Ping et al. | 164/4.1 |
| 5,328,502 A | * | 7/1994 | Backerud | 164/4.1 |
| 5,397,710 A | * | 3/1995 | Steinman | 422/56 |
| 5,482,866 A | * | 1/1996 | Denton et al. | 422/61 |
| 5,615,730 A | * | 4/1997 | Hiraoka et al. | 164/4.1 |
| 5,803,947 A | * | 9/1998 | Engell et al. | 420/129 |
| 5,804,006 A | * | 9/1998 | Kanno et al. | 148/511 |
| 5,968,833 A | * | 10/1999 | Furuta et al. | 422/61 |
| 6,132,531 A | * | 10/2000 | Fang et al. | 148/549 |
| 6,231,700 B1 | * | 5/2001 | Stone et al. | 148/686 |

* cited by examiner

*Primary Examiner*—Diego Gutierrez
*Assistant Examiner*—Yantza Guadalupe
(74) *Attorney, Agent, or Firm*—Bierman, Muserlian and Lucas

(57) ABSTRACT

The invention relates to a method for determining the magnesium content in molten aluminum alloy by thermal analysis by determining on a cooling curve the eutectic temperature, and substituting the above eutectic temperature in a formula of $Mg=\{(577-TE)/4.4\} \times Si/12.5$.

4 Claims, 2 Drawing Sheets

METHOD OF DETERMINING THE MAGNESIUM CONTENT IN MOLTEN ALUMINUM ALLOYS

FIELD OF THE INVENTION

This invention relates to a method of determining the magnesium content in molten aluminum alloys, and more particularly to a method for measuring the magnesium content in Al-Si aluminum alloy.

The magnesium content in molten aluminum, especially molten Al-Si aluminum alloys has a great influence in the strength of aluminum alloy products.

Al-7% Si-0.3% aluminum alloy which is usually utilized for making thin aluminum foil sheet contains about 0.3% by weight of magnesium in molten state. Tensile strength of the above aluminum alloy is about 28 Kg/mm2, but if the magnesium content is reduced to about 0.1% by weight, the tensile strength of this aluminum alloy decreases to about 15 Kg/mm2.

The chemical composition of the conventional aluminum alloys are standardized by JIS, ASTEM, AISI, SAE, BC, DIN, VDEh, NF, EN and ISO, and an analysis of the composition is affixed to the alloys. If the alloy is melted, the content of chemical composition other than magnesium (Mg) does not change, but the molten magnesium floats on the surface of the molten aluminum alloy magnesium and is finally oxidized so that the quantity of magnesium in the alloy will be decreased.

Usually, in order to prevent from the decrease of the content of magnesium in the aluminum alloy magnesium is added to the molten aluminum alloy.

For this purpose, however, it is necessary to measure the content of magnesium in the molten aluminum alloy before casting. To apply an emission spectrochemical analysis in order to measure the magnesium content in the aluminum alloy is very expensive and requires complicated operations.

Thus, in view of the above disadvantages, the main object of the present invention is to provide a simple method of determining the magnesium content in the molten aluminum alloys.

Another object of the invention is to provide a method for measuring the content of magnesium in aluminum alloy for the purpose to prevent deterioration of the quality of aluminum alloy products before casting.

SUMMARY OF THE INVENTION

In order to attain the above objects, a method for determining the magnesium content in molten aluminum alloy according to the present invention consists of steps of carrying out the thermal analysis of the molten alloy to obtain a cooling curve; measuring the eutectic temperature of the molten alloy from the cooling curve obtained; and determining the magnesium content in the molten aluminum alloy by using an equation prepared in advance.

According to the present invention, the molten aluminum alloy is poured into a sampling vessel which is usually used to measure a cooling curve in the thermal analysis.

A small amount, for example about 0.2 percent of weight of phosphorus (P) and/or sulphur (S) may be added into the vessel as the additive.

Further, Cu-P, Al-Cu-P and Zn-S or a mixture of these alloys may be used as the additive.

BRIEF DESCRIPTION OF THE DRAWINGS

A method of the present invention will be described with reference to an embodiment and the drawings, in which:

It is already known in the art that the eutectic temperature of Al-Si alloy is 577° C. as shown in FIG. 1. In a nonequilibrium state, however, the eutectic temperature depends on the amount (quantity) of the eutectic crystal in the molten aluminum alloy.

The eutectic crystal in the molten aluminum alloy is Al-P or Al-S, the amount of which is similar to silicate (Si) which is solidified at the eutectic temperature.

The amount of Al-P or Al-S in the molten aluminum alloy is not enough to congeal to the equilibrium solidification. Accordingly, the equilibrium temperature of Al-P or Al-S is lower than the temperature shown in the equilibrium diagram even if these aluminum alloys are in the supercooling condition for the reason that although the eutectic temperature of these alloys relate to the eutectic crystal, but is not related to the amount of the chemical composition. Consequently, it is very hard to measure the magnesium content in the above aluminum alloys from the eutectic temperature thereof.

In the light of the above, according to the present invention, a sufficient amount of phosphorus (P) or sulphur (S) is added into the molten aluminum alloy so that the eutectic temperature of the molten alloy may be related to the magnesium content therein.

The atomic weight of phosphorus (P=30.9736) is very close to the atomic weight of sulphur (S=32.06), and therefore the amount of P or S to be added to the molten aluminum alloy may be equalized.

Referring to an example, in which phosphorus (P) is added to the molten aluminum alloys.

As a general rule, in casting the aluminum alloys, a small amount, for example 30–100 ppm of sodium (Na) is added to the molten aluminum alloy in order to minimize the structure as a modification. If sodium is added to the molten aluminum alloy which is formed as to Al-P, in the beginning, phosphorous reacts with sodium (Na), and Al-P is decomposed so that there is fear of disappearance of eutectic crystal material therefrom.

According to the present invention, in considering the atomic weight of each of phosphorus (P) and sodium (Na), the amount of phosphorous corresponding to at least three (3) times as much as the amount of sodium that is 300 ppm of phosphorus is added to the molten aluminum alloy.

When a good enough quantity of eutectic crystal is presented in the molten aluminum alloy, the eutectic temperature of the molten alloy relates to the quantity of magnesium, and it will be calculated from the following experimental equation:

$$Mg=\{(577-TE)/4.4\} \times Si/12.5$$

in which 577 means 577° C. which is the eutectic temperature (TE) of Al-Si alloy in the content of Mg is zero;

(577−TE) shows the temperature difference between the eutectic temperature and an actually measured eutectic temperature.

A coefficient 12.5 is the composition of Al-Si alloy at the eutectic point.

EXPERIMENT

An alloy consisting of 99.9% Al-Si and Mg a sample in which the Si content is changed in the range of 2–12.5% and the Mg content is changed in the range of 0.1–1% are combined, and the contents of Si and Mg and eutectic temperature of each of the combined samples are measured. The results of the above are shown in FIG. 2.

Figure 1:
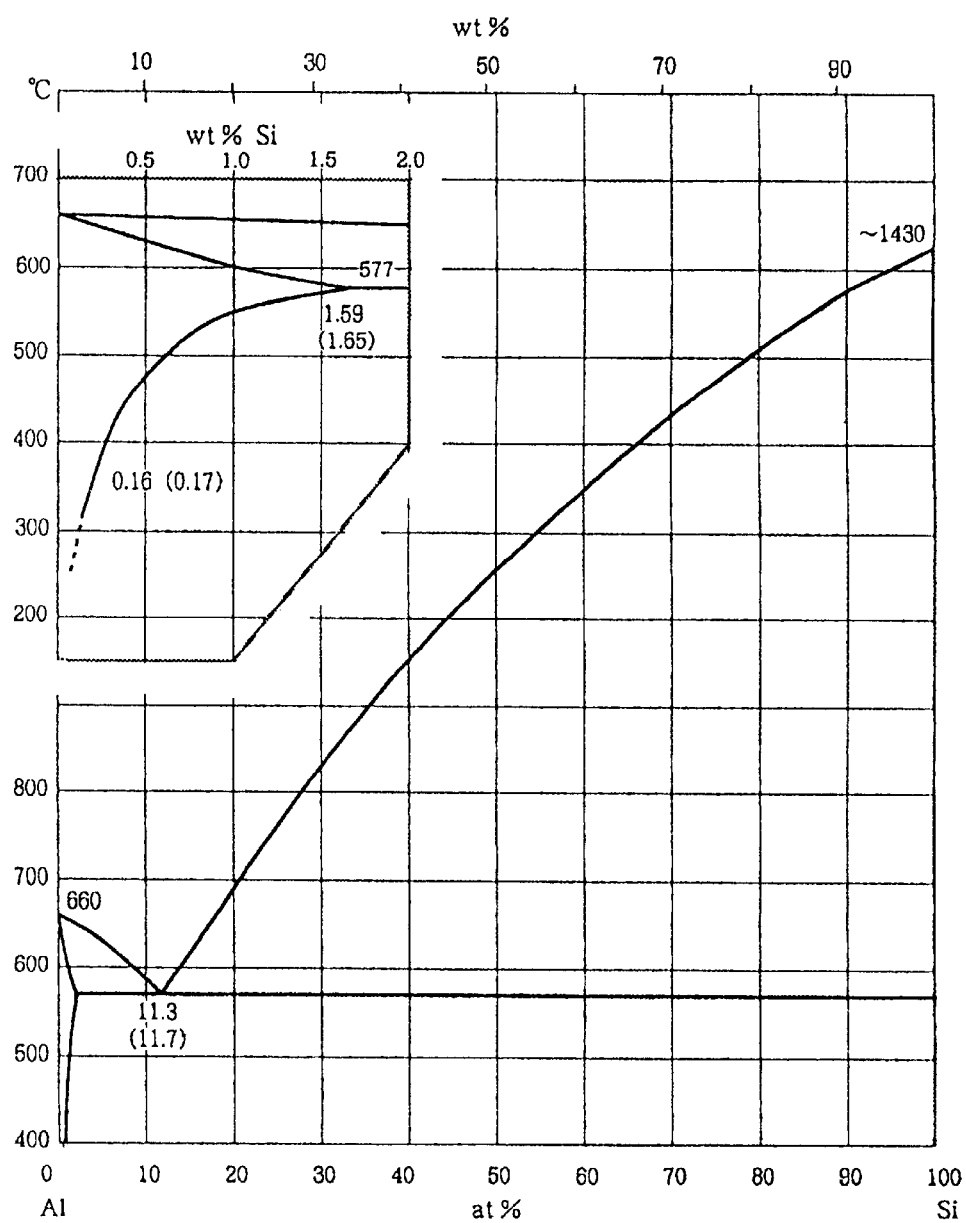
FIG. 1 shows an equilibrium diagram of Al-Si alloy.
Figure 2:
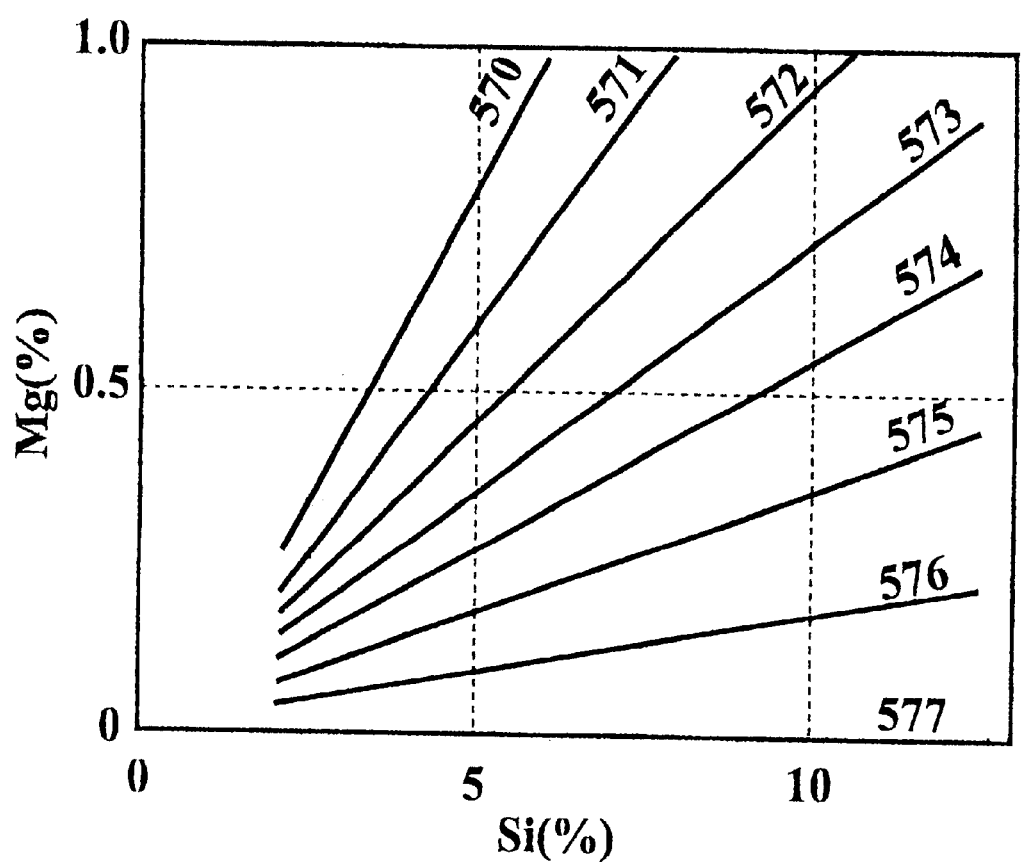
FIG. 2 shows the content of Si and Mg and the eutectic temperature of each of the samples which are tested by the method according to the present invention.

As shown in FIG. 2, if the eutectic temperature (TE) is 577° C., the content of magnesium (Mg) is 0%, and if it is 572.6° C. the content of Mg is 1%.

What is claimed is:

1. A method of determining the magnesium content in molten aluminum alloy comprising of steps of:

pouring molten aluminum alloy into a sampling vessel to be used for thermal analysis in order to obtain a cooling curve of said alloy;

confirming the eutectic temperature of said molten alloy; and substituting said eutectic temperature in a formula of $$Mg=\{(577-TE)/4.4\} \times Si/12.5.$$

2. A method as claimed in claim 1 in which phosphorus is added to said sampling vessel.

3. A method as claimed in claim 1 in which sulphur is added to said sampling vessel.

4. A method as claimed in claim 1 in which a mixture of phosphorus and sulphur is added to said sampling vessel.

* * * * *